(12) United States Patent
Dicarlo et al.

(10) Patent No.: US 7,722,580 B2
(45) Date of Patent: May 25, 2010

(54) PERCUTANEOUS ACCESS PORT

(75) Inventors: Paul Dicarlo, Middleboro, MA (US); Jeff Bean, Fitchburg, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 0 days.

(21) Appl. No.: 11/265,714

(22) Filed: Nov. 2, 2005

(65) Prior Publication Data
US 2007/0100302 A1  May 3, 2007

(51) Int. Cl.
*A61M 5/00* (2006.01)
(52) U.S. Cl. .............. 604/288.04; 604/288.01; 604/288.03; 604/502
(58) Field of Classification Search ........... 604/288.03, 604/288.01, 288.04, 502, 513
See application file for complete search history.

(56) References Cited

U.S. PATENT DOCUMENTS

| | | | |
|---|---|---|---|
| 4,983,162 A | * | 1/1991 | Metais et al. ........... 604/43 |
| 5,205,834 A | | 4/1993 | Moorehead et al. |
| 5,520,643 A | * | 5/1996 | Ensminger et al. ..... 604/288.03 |
| 6,607,504 B2 | * | 8/2003 | Haarala et al. ........... 604/93.01 |
| 6,764,472 B1 | * | 7/2004 | Burke et al. ........... 604/288.04 |
| 2003/0130627 A1 | * | 7/2003 | Smith et al. ........... 604/288.04 |
| 2004/0249361 A1 | | 12/2004 | Denoth et al. |
| 2004/0267238 A1 | * | 12/2004 | Haarala et al. ............. 604/502 |
| 2005/0171488 A1 | | 8/2005 | Weaver et al. |

FOREIGN PATENT DOCUMENTS

| | | |
|---|---|---|
| EP | 0 143 518 | 6/1985 |
| WO | 03/086527 | 10/2003 |

* cited by examiner

*Primary Examiner*—Nicholas D Lucchesi
*Assistant Examiner*—Laura A Bouchelle
(74) *Attorney, Agent, or Firm*—Bingham McCutchen LLP

(57) ABSTRACT

A percutaneous port comprises a port body defining a cavity and a first catheter channel adapted to allow passage of a catheter thereinto a shuttle removably received within the cavity, the shuttle including a first flow conduit which, when the shuttle is received within the cavity, extends to the first catheter channel and a sealing mechanism sealing the first flow conduit when a fluid pressure applied thereto is less than a threshold value and opening to permit flow therethrough when the fluid pressure applied thereto is at least the threshold value a cover releasably attachable to the port body to enclose the cavity.

6 Claims, 6 Drawing Sheets

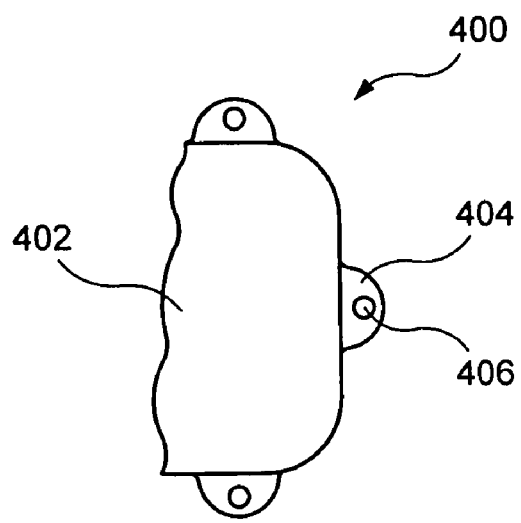
F I G. 10
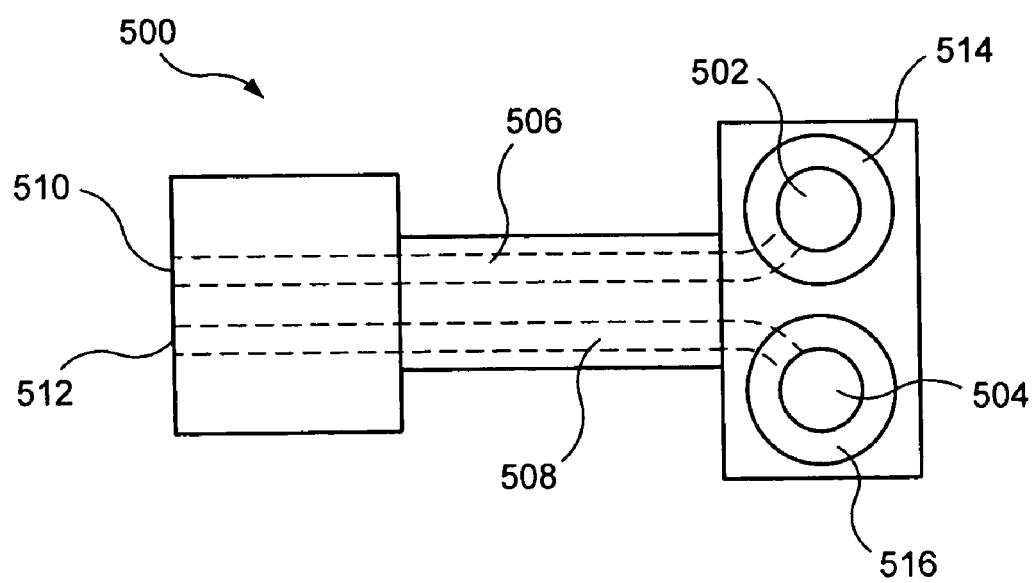
F I G. 11

US 7,722,580 B2

PERCUTANEOUS ACCESS PORT

BACKGROUND OF THE INVENTION

Treatments for chronic diseases often require repeated and prolonged access to the vascular system to, for example, provide therapeutic agents thereto and/or remove fluids therefrom. However, complications are associated with most of the various methods for providing this access.

SUMMARY OF THE INVENTION

The present invention is directed to a percutaneous port comprising a port body defining a cavity and a first catheter channel adapted to allow passage of a catheter thereinto and a shuttle removably received within the cavity, the shuttle including a first flow conduit which, when the shuttle is received within the cavity, extends to the first catheter channel in combination with a sealing mechanism sealing the first flow conduit when a fluid pressure applied thereto is less than a threshold value and opening to permit flow therethrough when the fluid pressure applied thereto is at least the threshold value and a cover releasably attachable to the port body to enclose the cavity.

BRIEF DESCRIPTION OF THE DRAWINGS

FIG. 10 is a top elevation view showing a different embodiment of a suture flange according to the invention; and FIG. 11 is a top elevation view showing an embodiment of a dual lumen port according to the present invention.

DETAILED DESCRIPTION

Figure 1:
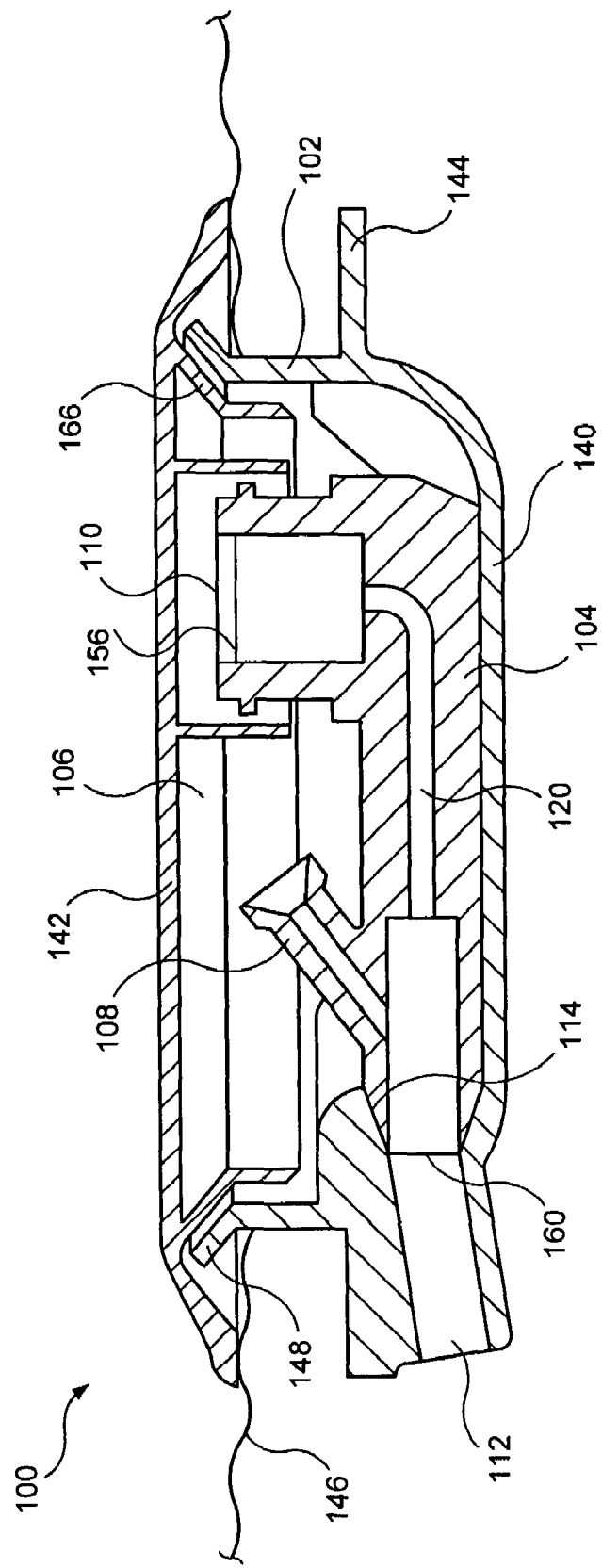
FIG. 1 is a cross sectional view showing an embodiment of a percutaneous access port according to the invention.
Figure 3:
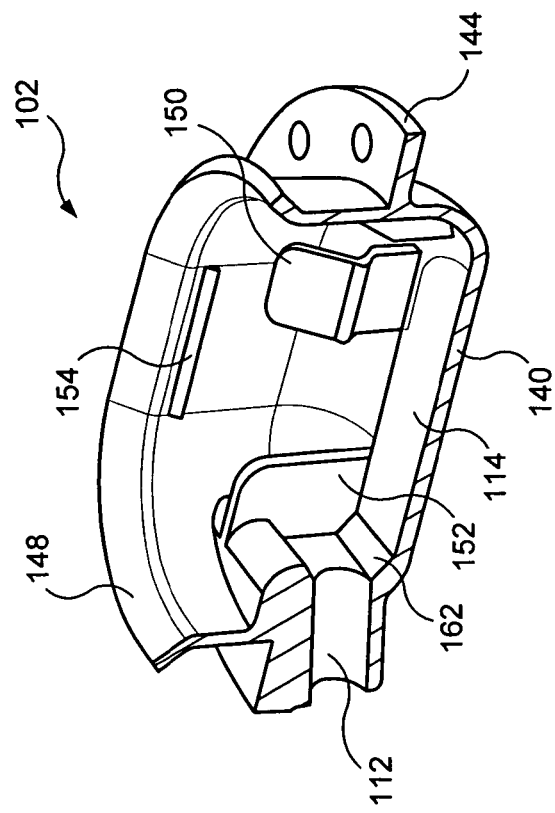
FIG. 3 is a perspective view showing a cross section of the port body of the percutaneous access port shown in FIG. 1.
Figure 2:
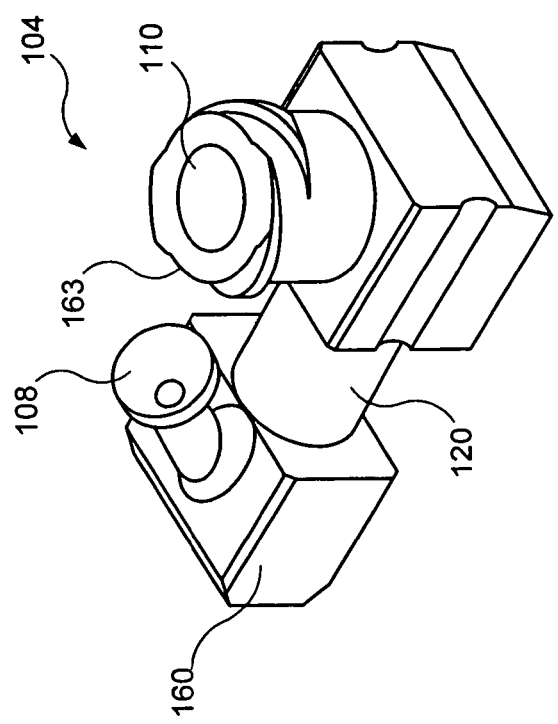
FIG. 2 is a perspective view of a shuttle of the percutaneous access port shown in FIG. 1.
Figure 4:
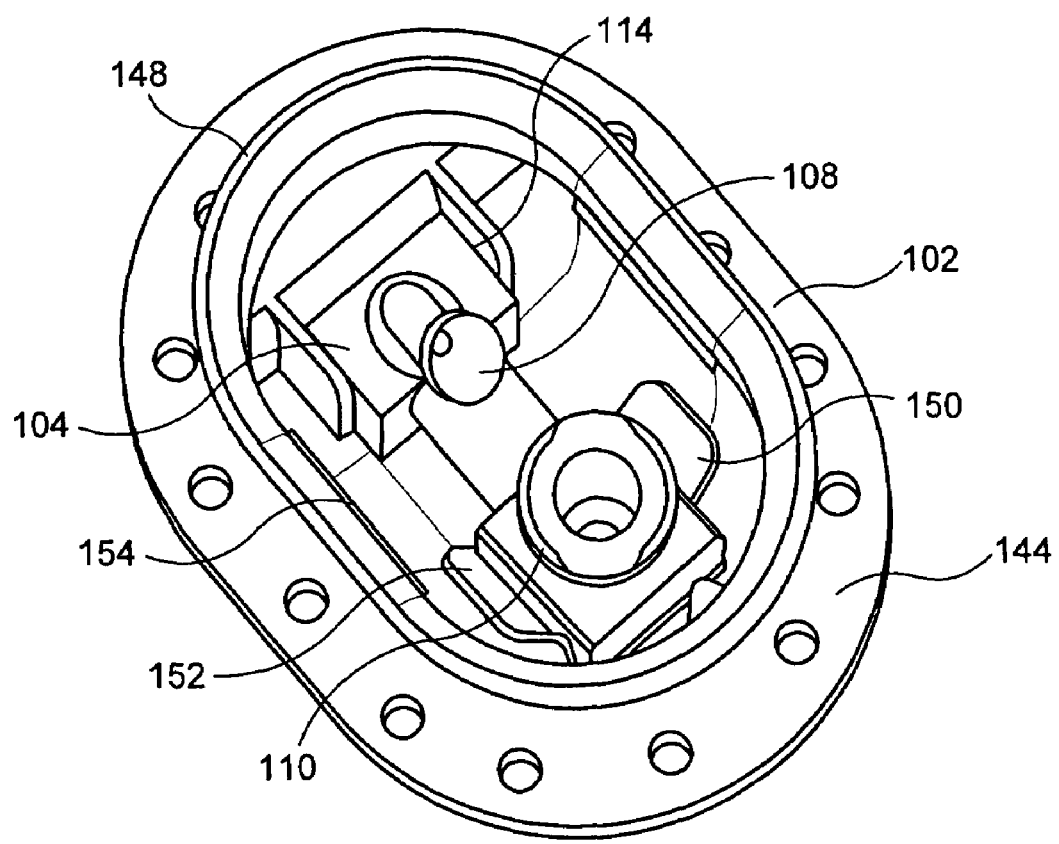
FIG. 4 is a perspective view of the shuttle in place within the port body shown in FIGS. 2 and 3.

The present invention may be further understood with reference to the following description and the appended drawings, wherein like elements are referred to with the same reference numerals. The invention relates to devices for accessing the body and, more specifically, devices for accessing the vascular system to add fluids thereto and/or remove fluids therefrom. On exemplary use of a device according to the invention is for treatments such as antibiotic therapies, hemodialysis access, chemotherapy regimens, etc. These treatments may last for a month or longer, and in some cases access to the body may be required for years.

Such long term access is often provided via a subcutaneous access port which is pierced by a needle which enters a reservoir of the port to introduce or withdraw fluids therefrom. The multiple punctures of the skin may cause patient discomfort and, in the long run, damage the skin causing the site of the port to become unusable. The large diameter needles used in procedures such as dialysis and chemotherapy may exacerbate these problems. In addition, the access port's reservoir may collect debris from the substances injected, coagulating blood or other sources, which may lead to an infection. Replacement or repair of the components of such a port and of the catheter(s) extending therefrom, requires a surgical procedure.

The various embodiments of the invention enhance the comfort, safety and convenience of the known systems for long term access of the vascular system. In one embodiment according to the invention, a percutaneous access port is provided, comprising a one way valve selectively sealing the port and an improved cover that securely locks in place to close an opening of the port. An additional feature of the exemplary port according to the invention is the ability to replace catheters extending therefrom without surgical intervention and without disturbing the port.

FIG. 1 shows an exemplary percutaneous port 100 according to the present invention which provides access to internal portions of the body, while minimizing the risk of infection, reducing patient discomfort and facilitating the replacement of catheters extending from the port 100. The exemplary port 100 comprises a port body 102 which is implanted with a majority of the port body 102 below a surface of the skin 146 and a bottom surface 140 of the port body 102 resting against tissue at the bottom of a surgically formed cavity.

Formed within the port body 102 are various passages and cavities including a catheter channel 112 for fluidly connecting to the port 102 a catheter (not shown), a distal end of which may be inserted to a target location within the body, for example within a blood vessel or other structure as desired. The catheter channel 112 is sized so that a proximal end of a catheter for use with the port 100 may pass therethrough toward a cavity 114 defined by the port body 102. Thus, depending on the shape and construction of the catheter, the entire catheter may be drawn through the catheter channel 112 and withdrawn from the body for repair or replacement.

The port body 102 comprises a flange 144 with perforations which may be employed as anchors for sutures or other fasteners to retain the port 100 in a desired position within the cavity. A removable shuttle 104 including a sealing mechanism (e.g., a PASV valve 110) and a guidewire valve bypass 108 is held in a desired position within the cavity 114 of the port body 102 by retaining elements 150, 152 which extend into the cavity 114. The retaining elements 150, 152 act on the shuttle 104 by, for example, friction, snap fit or any other suitable method of retaining the shuttle 104 in position. The user may manually release the retaining elements 150, 152 when necessary to remove the shuttle 104 from the port body 102, as will be described in more detail below. The retaining elements 150 and 152 are preferably dimensioned to minimize the size of the port body 102, while remaining large enough to be easily actuated by a user.

In a different embodiment, the flange 144 may be made smaller to reduce the overall dimensions of the port. For example, a port 400 shown in FIG. 10 has a flange 404 extending from a port body 402 thereof only around orifices 406, instead of completely surrounding the port 400. In addition, the port may be further reduced in size by reducing the number of orifices 406 to a minimum number necessary to stabilize the port 400.

As described above, the shuttle 104 is releasably held in place within the port body 102 by the retaining elements 150, 152 to provide a passage 120 to the inside of the body (e.g., to the vascular system) when the PASV 110 is open and to seal the passage 120 when the PASV 110 is closed. As would be understood by those skilled in the art, the passage 120 is placed in fluid communication with the vascular system (e.g., a blood vessel) via a catheter inserted into a distal end 160 of the shuttle 104 via the catheter channel 112. The distal end 160 of the shuttle 104 interfaces with a shuttle seat 162 of the port body 102 to form a fluid seal when the shuttle 104 is in place within the port body 102.

The PASV body 110 selectively provides access to the flow passage 120, and thus to the vascular system when desired and seals that passage when not in use. As would be understood by those skilled in the art, the PASV body 110 may, for example, include a valve membrane 156 sealing the passage at all times that a fluid pressure exerted thereagainst is no greater than a threshold pressure passes therethrough. When the pressure exerted against the valve membrane 156 is greater than the threshold pressure, the valve membrane 156 opens to permit fluid flow therethrough. The shuttle 104 preferably comprises an attachment 163 conforming to a conventional fluid connection used to couple the PASV body 110 to an external flow passage. During use to inject fluids, a fluid connection is made via the attachment 163 and fluid is injected through the connection at a pressure greater than the threshold pressure to open the valve membrane 156 so that the fluid passes through the PASV body 110 into the fluid conduit 120 to reach a target site (e.g., a body lumen into which a distal end of a catheter attached to the conduit 120 is inserted). As would be understood by those skilled in the art, flow through the PASV body 110 may be reversed to remove fluids by applying to the connection a negative pressure greater in magnitude than the threshold pressure.

As described above, the shuttle 104 preferably also comprises a guidewire valve bypass 108 allowing a guidewire to be inserted into a catheter attached to the catheter channel 112 without damaging the valve 110. Those skilled in the art will understand that the guidewire may be used to aid in implanting the catheter at a desired location and to otherwise assist in the correct positioning of components of the system within the body. The guidewire valve bypass 108 may also be used to insert a guidewire to the target site during replacement of a defective or damaged catheter to facilitate the positioning of a replacement catheter at the target site as more fully described below. A cap is inserted over the guidewire valve bypass 108 to seal it when not in use to prevent contaminants from reaching the vascular system.

In a different embodiment, the shuttle 104 may be designed without the guidewire valve bypass 108. In this embodiment, the valve body 110 allows a guidewire to be passed therethrough without sustaining damage. For example, the membrane of a PASV valve may be reinforced to improve its ability to withstand repeated entry by the guidewire (e.g., when the port 100 and the catheter are implanted). By omitting the guidewire valve bypass it is possible to manufacture a percutaneous port having smaller dimensions, which is easier to implant.

One advantage of the port 100 according to the invention is that the catheter attached to the catheter channel 112 may be replaced without removing the port and without performing a complex surgical procedure. In case of failure or other damage to the catheter, a guide wire may be inserted through the catheter to the target site via the guide wire valve bypass 108. The shuttle 104 may then be removed from the port body 102 over the guide wire to allow free access to the proximal end of the catheter via the now empty cavity 114. The catheter may then be removed through the catheter channel 112 over the guide wire without disturbing the port body 102. A new catheter may then be reinserted over the guide wire through the catheter channel 112 to the target site. The guide wire may then be removed and the shuttle 104 may be repositioned in the cavity 114 and attached to the proximal end of the catheter to form a fluid tight seal with the shuttle seat 162 and with the catheter. A locking mechanism is preferably provided on the shuttle seat 162 to lock the catheter in place after insertion.

In the exemplary embodiment shown, the cavity 114 of the port body 102 is sealed by a cover 106 which prevents contaminants from entering the port 100. For example, the cover 106 is preferably securely locked in place over the port body 102 when not in use to prevent inadvertent removal therefrom. The port body 102 according to this exemplary embodiment comprises a lip 148 cooperating with protrusions 166 of the cover 106 to form a snap or frictional attachment thereto with the lip 148 substantially flush with the skin 146 of the patient, so that an upper surface 142 of the cover 106 protrudes only minimally above a surface if the skin. This feature makes the port 100 more easily tolerated by the patient and less likely to be inadvertently dislodged during normal patient activity. As would be understood, additional internal snaps or ridges 154 may be formed on the port body 102 to better retain the cover 106 in place.

A relatively large free space is formed between the cavity 114 of the port body 102 and the cover 106. This free space may preferably be filled with an antibacterial agent residing in the port 100 between uses, to help prevent the establishment of an infection. Thus the cover 106, which also acts as a fluid seal, and a gasket seal between the cover 106 and port body 102, act to prevent the antibacterial agent from leaking out of the port 100 and onto the patient. The valve 156 of the PASV valve body 110 and the cap covering the guidewire valve bypass 108 prevent the antibacterial agent from reaching the bloodstream.

Figure 6:
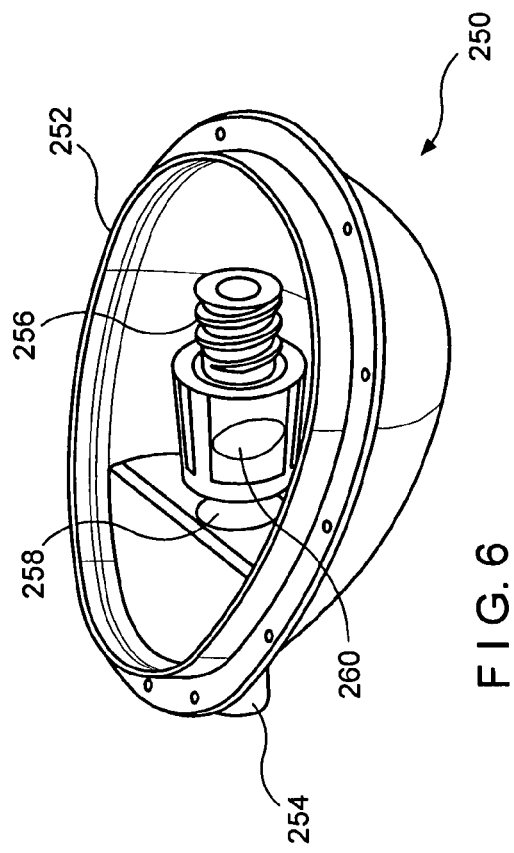
FIG. 6 is a perspective view of a third embodiment of the percutaneous access port according to the invention.
Figure 5:
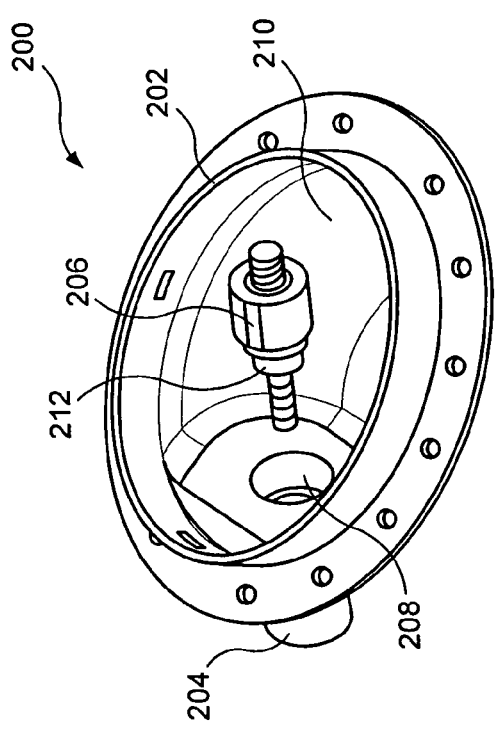
FIG. 5 is a perspective view of a second embodiment of the percutaneous access port according to the invention.

FIGS. 5 and 6 show two additional embodiments of a percutaneous port according to the invention. The port 200 of FIG. 5 comprises a port body 202 including an opening 208 connected to a catheter channel 204. In this exemplary embodiment, a catheter enters the port body 202 through the catheter channel 204 so that a fluid connection may be made between the catheter and an external fluid conduit, to infuse and/or remove fluids from the patient. As described above, a removable shuttle including a selective sealing mechanism such as a PASV 206 is removably insertable within the opening 208 to seal the catheter channel 204 when not in use. A seal 212 extends from the distal end of the shuttle which sealingly engages the opening 208 without requiring any additional components.

The shuttle of the embodiment shown in FIG. 5 includes a valve 206 which may be easily removed and exchanged for a new one if it becomes damaged or clogged. The PASV valve 206 may be replaced without removing the entire port 200, and without the need to perform a surgical procedure. The procedure is simplified because the seal 212 is a part of the PASV 206 so that the surgeon does not have to manipulate an additional sealing component to assemble the port 200. The catheter may still be withdrawn through the opening 208.

FIG. 6 shows another embodiment of the port according to the invention. In this case, the valve 256 of the percutaneous port 250 does not include an integral sealing element, but instead uses a separate sealing element. For example, a carrying unit 260 fits around the valve 256 to form a fluid tight seal between the valve 256 and the opening 258 leading to the catheter and a catheter channel 254 allows the catheter to partially enter into the port body 252 of the port 250. The addition of the carrying unit 260 provides a sealing fit with the port body 252 and allows the use of a valve 256 of conventional design. The use of conventional components, in turn, provides a simpler and less expensive port 250.

Figure 7:
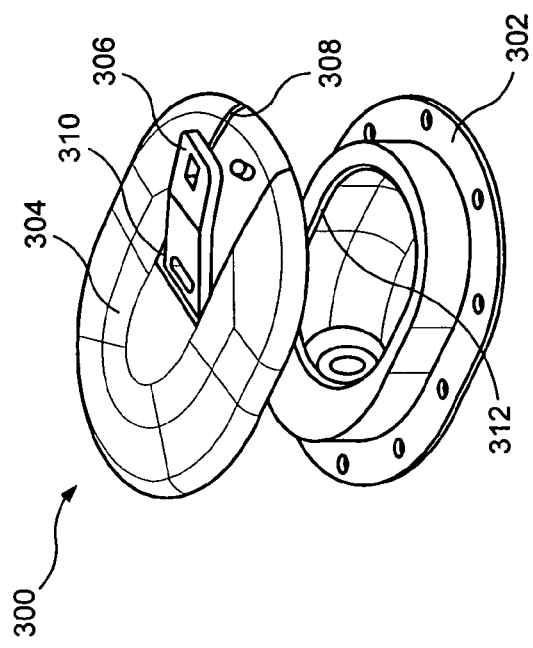
FIG. 7 is a perspective view of an embodiment of a locking lid for a percutaneous access port according to the invention.
Figure 9:
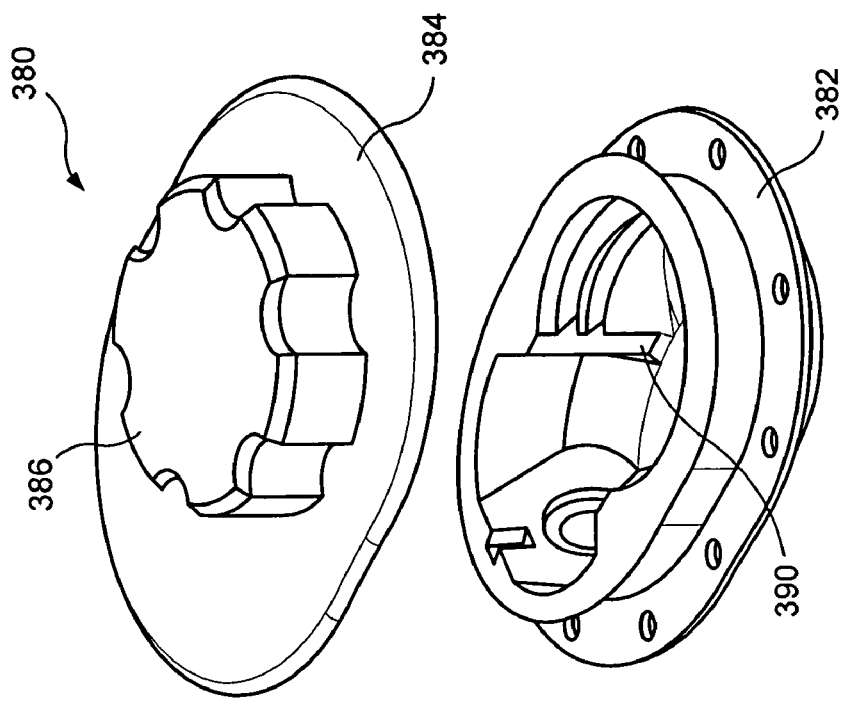
FIG. 9 is a perspective view of a different embodiment of a locking lid for a percutaneous access port according to the invention.
Figure 8:
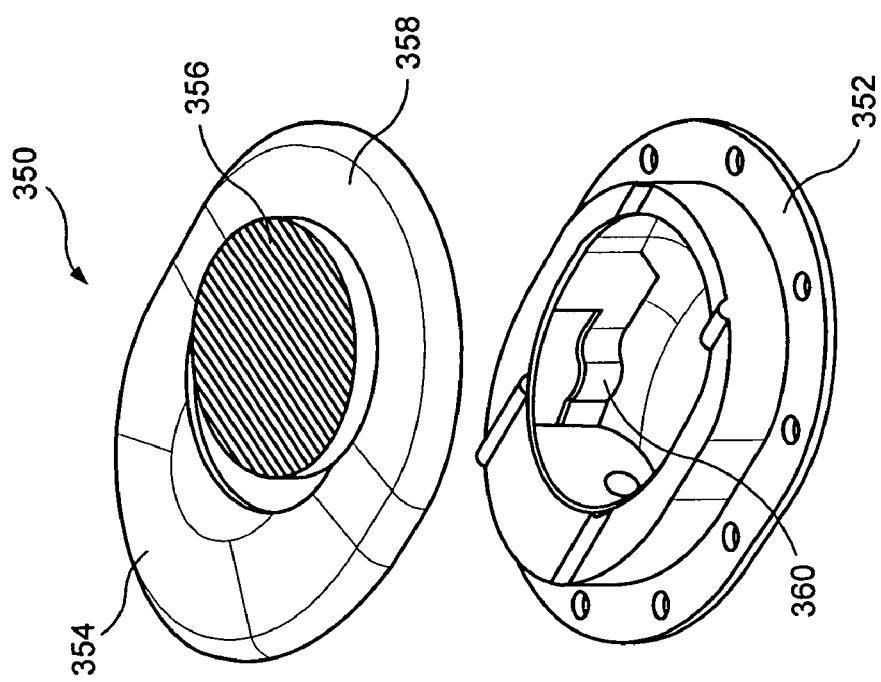
FIG. 8 is a perspective view of another embodiment of a locking lid for a percutaneous access port according to the invention.

As described above, the cover of the percutaneous port according to the invention is adapted to prevent its inadvertent removal. The locking mechanism for the cover thus is designed to resist detachment due to impact, handling by the patient and/or from movement and forces to which it is exposed during normal patient activity. Various exemplary designs of the cover according to the invention are shown in FIGS. 7, 8 and 9. FIG. 7 shows a percutaneous port 300 comprising a port body 302 closed by a cover 304. The cover 304 has a mechanical locking mechanism actuated by manually moving a tab 306 about a pivot point 310. For example, the tab 306 may be linked to prongs 308 that extend into a groove or indentation 312 to lock the cover 304 in place. The tab 306 may be held into the locked position by an overcenter linkage, until raised manually by the user.

As shown in FIG. 8, a port 350 according to another embodiment is shown in FIG. 8 includes a cover 354 that releasably attachable to the port body 352 by a mechanical latch. For example, the cover 354 includes a sliding lock/release actuator 356 which, when actuated, moves a mechanical linkage that activates locking protrusions 358 to engage slots 360 formed on the port body 352. The actuator 356 may be thumb operated by the user to slide between locked and unlocked positions.

As shown in FIG. 9, a port 380 according to a further embodiment includes a port cover 384 closing a port body 382. The port cover 384 has no moving parts, but instead releasably locks on the port body 382 by frictional engagement with grooves 390. A grasping element 386 may optionally be provided to allow a user to grasp the cover 384 and to exert a force thereto sufficient to overcome the frictional engagement with the grooves 390. The port cover 384 can be screwed in to the port body 382 as well. The cover 384 of the exemplary port 380 is inexpensive and relatively easy to manufacture because of the absence of moving parts.

The percutaneous port according to the present invention may also be constructed with dual lumens allowing, for example, for simultaneous inflow and outflow of fluids via a dual lumen catheter. As shown in FIG. 11, a dual lumen percutaneous port including a dual lumen shuttle 500 includes inflow and outflow fluid passages 506, 508, respectively, extending therethrough between an 510 inlet and an outlet 512, respectively, each of which is adapted to sealingly mate in fluid connection with respective catheters. As described above, the shuttle 500 may be connected to a percutaneous port during operation, and may be detached and removed from the percutaneous port to replace one or both catheters, without having to perform a complex surgical procedure.

In the exemplary embodiment shown, each of the fluid passages 506, 508 has a proximal opening into a corresponding one of a pair of valve bodies 514, 516 each of which is adapted to seal the catheter when fluids are not being injected or withdrawn therefrom with each of the valve bodies 514, 516 comprising, for example, a PASV valve membrane 502, 504, respectively, designed to allow the passage of a guidewire therethrough without sustaining damage. Accordingly, it is not necessary to provide one or more guidewire valve bypass ports and the shuttle 500 may be made smaller and more compact. The side by side orientation of the valve bodies 514 and 516 also promotes a compact size, which results in simpler implantation and use of the port. In other embodiments, a guidewire valve bypass similar to that shown in FIG. 1 may be included to further reduce damage to the valve membranes 502, 504.

Furthermore, as would be understood by those skilled in the art a gasket seal (not shown) is included between the port bodies and the covers of the various embodiments to aid in preventing antibacterial agent from leaking from the port bodies.

The present invention has been described with reference to specific embodiments, and more specifically to a percutaneous vascular access port. However, other embodiments may be devised that are applicable to other medical devices and procedures, such as accessing other body lumens and drainage of fluids from the body. Accordingly, various modifications and changes may be made to the embodiments, particularly with regard to dimensions and materials, without departing from the broadest spirit and scope of the present invention as set forth in the claims that follow. The specification and drawings are accordingly to be regarded in an illustrative rather than restrictive sense.

What is claimed is:

1. A method comprising:
   connecting a catheter to a percutaneous port;
   removing a cover of the percutaneous port to access a cavity therein;
   detaching a shuttle from the port to access a catheter channel of the port wherein, coupled to the port, a flow conduit of the shuttle is in fluid communication with the catheter channel, the flow conduit remaining sealed at all times when a fluid pressure applied thereto remains below a threshold value;
   extracting the catheter from the port through the catheter channel;
   inserting a new catheter to a target site within the body though the catheter channel;
   attaching the shuttle to the port so that the flow conduit is in fluid connection with the catheter; and
   closing the percutaneous port with the cover.

2. The method according to claim 1, further comprising inserting a guidewire through a valve bypass of the shuttle.

3. The method according to claim 1, further comprising inserting a guidewire through a valve body of the shuttle.

4. The method according to claim 1, further comprising stabilizing the percutaneous port with sutures inserted through orifices of a flange of the port.

5. The method according to claim 1, further comprising filling the cavity with an antibacterial compound.

6. The method according to claim 1, further comprising attaching the catheter to the catheter channel.

* * * * *